(12) United States Patent
Tanaka et al.

(10) Patent No.: US 6,955,667 B1
(45) Date of Patent: Oct. 18, 2005

(54) ABSORBENT ARTICLE

(75) Inventors: Masahito Tanaka, Tochigi (JP);
Mayumi Kimura, Tochigi (JP); Takao
Nakayama, Tochigi (JP); **Mitsugu
Hamajima, Tochigi (JP); Minoru
Nakanishi**, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/147,894

(22) PCT Filed: Oct. 22, 1997

(86) PCT No.: PCT/JP97/03816

§ 371 (c)(1),
(2), (4) Date: Mar. 23, 1999

(87) PCT Pub. No.: WO98/17217

PCT Pub. Date: Apr. 30, 1998

(30) Foreign Application Priority Data

Oct. 23, 1996 (JP) .................................. 8/281119

(51) Int. Cl.⁷ ........................... A61F 13/15; A61F 13/20
(52) U.S. Cl. ................. 604/385.24; 604/366; 604/368; 604/375; 604/378; 604/385.03; 604/385.101; 604/387
(58) Field of Search ................. 604/365, 366, 604/868, 369, 378–382, 385.01, 385.101, 604/385.12, 385.14, 355.17, 385.21, 385.23, 604/385.3, 387, 393, 394, 385.03, 385.04, 604/385.201, 396–402

(56) References Cited

U.S. PATENT DOCUMENTS 2,331,355 A * 10/1943 Strongson .............. 604/385.17
2,566,451 A * 9/1951 Julien ..................... 604/380
3,211,147 A * 10/1965 Pherson et al. ........... 604/378
3,364,931 A * 1/1968 Hirsch ..................... 604/366
3,572,342 A * 3/1971 Lindquist et al. .......... 604/369
3,575,174 A * 4/1971 Mogor .................. 604/385.01
3,699,966 A * 10/1972 Chapuis ..................... 604/378
3,736,931 A 6/1973 Glassman
3,744,494 A * 7/1973 Marsan ..................... 604/378
4,029,101 A 6/1977 Chesky et al.
4,041,950 A * 8/1977 Jones, Sr. .............. 604/385.28
4,410,324 A * 10/1983 Sabee .................... 604/385.21
4,608,047 A 8/1986 Mattingly
4,704,115 A * 11/1987 Buell .................... 604/385.26
4,731,071 A * 3/1988 Pigneul ..................... 604/368
4,753,644 A * 6/1988 Cottenden et al. .......... 604/378
4,790,839 A * 12/1988 Ahr ........................... 604/378
4,988,344 A * 1/1991 Reising et al. .............. 604/380
5,211,641 A 5/1993 Roos et al.
5,318,553 A * 6/1994 Weeks et al. ............... 604/378
5,342,337 A * 8/1994 Runeman et al. ........... 604/370
5,368,926 A 11/1994 Thompson et al.
5,380,310 A * 1/1995 Mitrani .................... 604/347
5,405,342 A * 4/1995 Roessler et al. ......... 604/385.14

(Continued)

FOREIGN PATENT DOCUMENTS

CA          121512          6/1995

(Continued)

Primary Examiner—Karin Reichle
(74) Attorney, Agent, or Firm—Birch, Stewart, Kolasch & Birch, LLP

(57) ABSTRACT

An absorbent article includes a liquid-permeable top layer, a liquid-impermeable back layer, and a liquid retentive absorbent member, interposed between the top layer and the back layer. The absorbent member is arranged to form an opposing pair of barrier cuffs which are within longitudinal edges of the top layer and extend along the longitudinal edges. A pocket portion is formed between the pair of barrier cuffs.

18 Claims, 8 Drawing Sheets

U.S. PATENT DOCUMENTS

| | | | | | |
|---|---|---|---|---|---|
| 5,417,680 | A | * | 5/1995 | Kimura et al. | 604/385.28 |
| 5,489,282 | A | * | 2/1996 | Zehner et al. | 604/385.26 |
| 5,578,025 | A | * | 11/1996 | May | 604/368 |
| 5,601,544 | A | | 2/1997 | Glaug et al. | |
| 5,624,423 | A | | 4/1997 | Anjur et al. | |
| 5,681,303 | A | * | 10/1997 | Mills et al. | 604/385.26 |
| 5,704,928 | A | * | 1/1998 | Morita et al. | 604/387 |
| 5,713,885 | A | * | 2/1998 | Jorgenson et al. | 604/385.201 |
| 5,735,838 | A | * | 4/1998 | Ronnberg et al. | 604/385.28 |
| 5,795,344 | A | * | 8/1998 | Chappell | 604/379 |
| 5,814,036 | A | * | 9/1998 | Ronnberg et al. | 604/385.201 |
| 5,827,254 | A | * | 10/1998 | Trombetta et al. | 604/378 |
| 5,954,705 | A | * | 9/1999 | Sawaki et al. | 604/378 |
| 6,159,190 | A | * | 12/2000 | Tanaka et al. | 604/385.24 |
| 6,293,935 | B1 | * | 9/2001 | Kimura et al. | 604/387 |
| 6,326,525 | B1 | * | 12/2001 | Hamajima et al. | 604/378 |
| 6,432,094 | B1 | * | 8/2002 | Fujioka et al. | 604/385.01 |
| 6,551,297 | B2 | * | 4/2003 | Tanaka et al. | 604/385.24 |

FOREIGN PATENT DOCUMENTS

| | | | | |
|---|---|---|---|---|
| EP | 0219326 | | 4/1987 | |
| EP | 0 483 592 | | 5/1992 | |
| EP | 0 472 633 | | 2/1993 | |
| EP | 0 532 035 | | 5/1993 | |
| EP | 0549988 | | 7/1993 | |
| EP | 0558889 | | 9/1993 | |
| GB | 1164492 | * | 9/1969 | 604/380 |
| GB | 2 135 892 | | 9/1984 | |
| GB | 2267873 | * | 7/1993 | 604/393 |
| JP | 2-61326 | | 5/1990 | |
| JP | 3-123553 | * | 5/1991 | |
| JP | 4-282153 | | 10/1992 | |
| JP | 4-506022 | | 10/1992 | |
| TW | 286541 | | 9/1996 | |
| WO | 9109582 | * | 7/1991 | 604/378 |
| WO | 95/16422 | | 6/1995 | |
| WO | 95/31163 | | 11/1995 | |
| WO | 9620679 | | 7/1996 | |
| WO | 9640029 | | 12/1996 | |

* cited by examiner

ABSORBENT ARTICLE

This application is the national phase under 35 U.S.C. §371 of PCT International Application No. PCT/JP97/03816 which has an International filing date of Oct. 22, 1997 which designated the United States of America.

TECHNICAL FIELD

This invention relates to an absorbent article, such as a sanitary napkin, an incontinent pad, breastfeeding pad, and the like, including a liquid-permeable top layer, a liquid-impermeable back layer, and a liquid-retentive absorbent core disposed between the top layer and the back layer. More particularly, the present invention is directed to an absorbent article which is capable of preventing liquid leakage irrespective of the quantity of body fluid and motion of the wearer.

BACKGROUND ART

In general, absorbent articles such as a sanitary napkin, an incontinent pad, breastfeeding pad, and the like are known to include a liquid-permeable top layer, a liquid-impermeable back layer, and a liquid-retentive absorbent core disposed between the top layer and the back layer. Such an absorbent article is required to cause body fluid, such as blood, urine, and the like, to rapidly migrate to the absorbent core where it is absorbed and retained with no leakage.

In order to absorb and retain body fluid with no leakage, heretofore, there has been utilized an absorbent article, in which a liquid-preventive will is formed on each of the width-wise, left and right side portions so as to prevent leakage of unabsorbed body fluid deposited on the surface of the top layer. These leakage-preventive walls are formed by using a topsheet which constitutes the top layer of the absorbent article and a backsheet which constitutes the back layer, or by alternatively using a nonwoven fabric and a film-like material.

However, since such a liquid-preventive wall of the absorbent article either has no liquid absorbing/retentive properties or has only small liquid absorbing/retentive properties, body fluid tends to leak beyond the leakage-preventive walls when a large quantity of body fluid is deposited on the surface of the top layer, caused by motion of the user, or the like.

It is, therefore, an object of the present invention, to provide an absorbent article which is capable of preventing the possible leakage of body fluid in a reliable manner, irrespective of the quantity of body fluid and motion of the wearer.

SUMMARY OF THE INVENTION

The present invention has achieved the above objects by providing an absorbent article comprising: a liquid-permeable top layer; a liquid-impermeable back layer; a liquid retentive absorbent member, interposed entirely between said the top layer and said the back layer, wherein the said absorbent member is being arranged to form (a) an opposing pair of barrier cuffs which are within longitudinal edges of said top layer and extend along the longitudinal edges, said absorbent member containing a single absorbent sheet, said pair of barrier cuffs being formed by integrally folding only the single absorbent sheet and said top layer, and (b) a pocket portion formed between said pair of barrier cuffs; and a projecting portion located between said barrier cuffs on a skin contactable surface side of said pocket portion along the longitudinal direction of said barrier cuffs, said projecting portion being formed by an absorbent pad, wherein said absorbent sheet has a thickness of 0.3 mm to 5 mm.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Several embodiments of the absorbent article of the present invention will now be described specifically with reference to the drawings. In any one of the first to seventh embodiments, a liquid-permeable top sheet is used as a top layer and a liquid-impermeable back sheet is used as a back layer.

Figure 1:
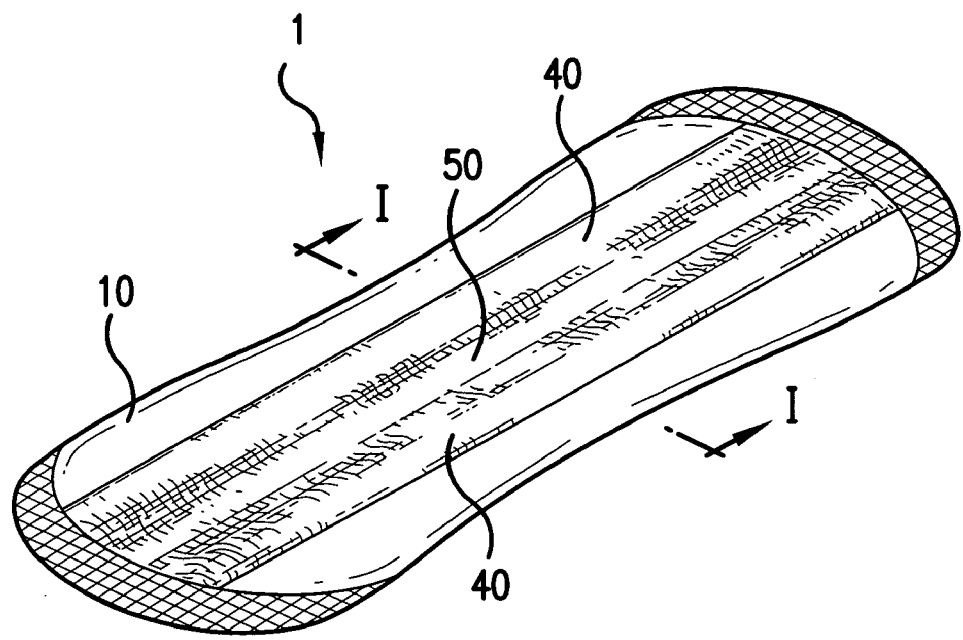
FIG. 1 is a perspective view showing an absorbent article according to a first embodiment of the present invention.
Figure 2:
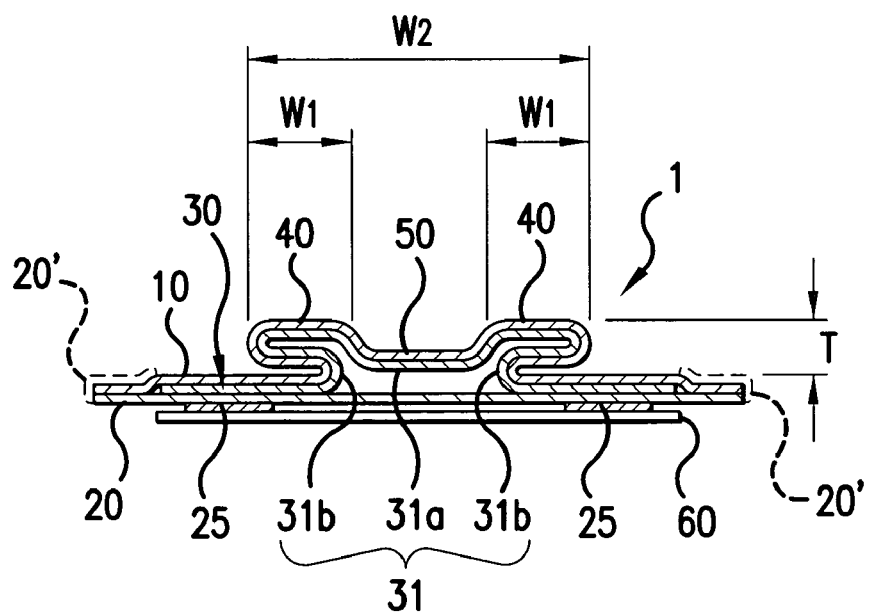
FIG. 2 is a sectional view taken along line I—I of FIG. 1, and viewed in a direction as indicated by arrows.

FIG. 1 is a perspective view showing a sanitary napkin as the first embodiment of an absorbent article of the present invention, and FIG. 2 is a sectional view, taken along line I—I of FIG. 1 and viewed in a direction as indicated by arrows.

A sanitary napkin 1 according to this embodiment includes a liquid-permeable top layer 10, a liquid-impermeable back layer 20, and a liquid-retentive absorbent member 30 interposed between the top layer 10 and the back layer 20. This construction is the same as the prior art.

As shown in FIG. 1 or 2, in the sanitary napkin 1 according to this embodiment, the absorbent member 30 is arranged to form an opposing pair of absorbent barrier cuffs 40, 40 which are within the longitudinal edges of the top layer 10 and extend along the longitudinal edges, and to form a pocket portion 50 between the pair of barrier cuffs 40, 40.

This embodiment will now be described in more detail. The absorbent member 30 comprises an absorbent sheet 31 having a thickness of 0.3 mm to 5 mm. The absorbent sheet 31 is formed by bending a sheet which comprises a central portion 31a and a pair of side portions 31b, 31b each connected to each opposing side of the central portion 31a. The side portions 31b,31b are folded back to the back layer 20 side at the opposing sides of the central portion 31a and then further folded back so as to be overlaid upon the back layer 20. The side portions 31b, 31b are arranged opposite and away from each other on the back layer 20 side of the central portion 31a. Free edge portions of the side portions 31b, 31b are each arranged in the vicinity of each of the left and right opposing side edges of the back layer 20. The absorbent sheet of the barrier cuffs 40,40 is folded in an overlapping, serpentine configuration. The folding portions of the absorbent sheet 31 are located along the longitudinal direction of the sanitary napkin 1 and overlaid in multiple layers at prescribed distant locations from the left and right opposing side edges of the top layer 10.

Almost an entire surface of the absorbent sheet 31 is overlaid by the top layer 10, and the absorbent sheet 31 and the top layer 10 are folded integrally. The above-mentioned barrier cuffs 40, 40 are formed by the absorbent sheet 31 and the top layer 10. In other words, the absorbent article includes means for attaching the top layer 10 to the liquid retentive member 30 (the absorbent sheet 31). The overlaid structure of the absorbent sheet 31 and top sheet 10 may be achieved by attachment using an adhesive agent or heat sealing, aside from a simple placement of the top layer 10 upon the absorbent sheet 31. The barrier cuffs 40, 40 are located apart from each other and the above-mentioned pocket portion 50 is formed therebetween. The absorbent member 30 (the absorbent sheet 31) includes means for attaching portions adjacent the barrier cuffs 40,40 (i.e. portions which are located outside the barrier cuffs 40,40) to the back layer 20. The barrier cuffs 40,40 are spaced apart from the back layer 20. The means for attaching the portions adjacent the barrier cuffs 40, 40 to the back layer 20 includes at least one of an adhesive agent and heat sealing.

The top layer 10 is extended to a perimeter of the absorbent sheet 31 and secured to the back layer 20 at the perimeter of the absorbent sheet 31.

The back layer 20 is applied at its outer surface (clothing contacting surface when the sanitary napkin is worn) with a viscous agent to thereby form two viscous portions 25, 25 in the longitudinal direction of the back layer 20. The viscous portions 25, 25 are each covered with a peelable paper 60. This peelable paper 60 is peeled off immediately before the sanitary napkin 1 is worn, so that the viscous portions 25, 25 are exposed. The viscous portions 25, 25, when worn, are adhered to the clothing in order to prevent slippage of the sanitary napkin 1.

The thickness of sheet 31 is preferably 0.3 mm to 5 mm, more preferably 0.3 mm to 3 mm, and most preferably 0.3 mm to 1.5 mm. If the thickness is less than 0.3 mm, it is difficult to provide the barrier cuffs 40, 40 capable of sufficiently exhibiting the effects of the present invention such as improved fitness, and an increased capacity for absorbing a body fluid. In addition, the sheet 31 tends to become twisted when folded. In contrast, if the thickness is more than 5 mm, the rigidity of the absorbent sheet 31 is overly increased which spoils the fitness. Thus, the desired effect cannot be obtained and the perception of disorder is given to the wearer.

Figure 16:
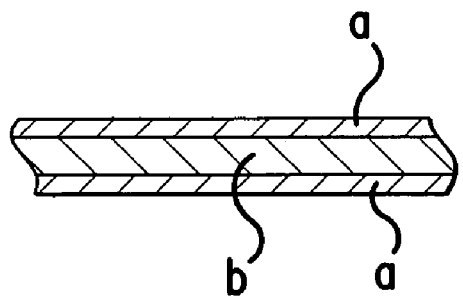
FIG. 16 is a sectional view of one embodiment of the absorbent member according to the present invention.

The absorbent sheet 31 can be absorbent paper, nonwoven fabric, a pulp sheet made of fibers and a binder, fluff pulp, a sheet obtainable by interposing a superabsorbent polymer b between a pair of paper or nonwoven fabric a (see FIG. 16), a sheet made of a mixture of a fiber (especially, hydrophilic fiber), a binder and a superabsorbent polymer, and the like. A sheet obtained by admixing a superabsorbent polymer and fiber is preferred for its absorptivity for body fluid. The superabsorbent polymer in such a sheet may be dispersed either in layers or in three dimensions.

The above-described material forming the absorbent sheet 31 preferably includes a cellulose fiber, such as wood pulp; a regenerated cellulose fiber, such as viscous rayon and cuprammonium rayon; a synthetic hydrophilic fiber, such as polyvinyl alcohol fiber and polyacrylonitrile fiber; and a synthetic fiber with the surface thereof rendered hydrophilic with a surface active agent, etc. such as polyethylene fiber, polypropylene fiber, polyethylene terephthalate fiber, polyethylene/polypropylene conjugate fiber, and polyethylene/polyethylene terephthalate conjugate fiber. Cellulose fibers are preferred for their satisfactory retention of hydrophilic properties.

The superabsorbent polymer which can be admixed with the absorbent sheet 31 is preferably one capable of absorbing and retaining 20 or more times as much liquid as its own weight and gelling upon liquid absorption. Such superabsorbent polymers include starch, crosslinked carboxymethylated cellulose, polyacrylic acid or a salt thereof, and a polyacrylate graft polymer. The polyacrylate is preferably sodium polyacrylate. Acrylic acid copolymers containing a comonomer, such as maleic acid, itaconic acid, acrylamide, 2-acrylamide-2-methylpropanesulfonic acid, 2-(meth)acryloylethanesulfonic acid, 2-hydroxyethyl (meth)acrylate or styrenesulfonic acid, in such a proportion that does not impair its performance as a superabsorbent polymer, can also be preferably used.

Particularly preferred are superabsorbent polymers capable of absorbing and retaining a large quantity of liquid through ionic osmosis and yet having no leaks even under pressure, comprising water-insoluble and hydrophilic crosslinked polymer particles which are obtained by polymerizing acrylic acid or an alkali salt thereof (e.g. sodium or potassium), etc. followed by crosslinking for water insolubilization.

A preferred absorbent sheet 31 is the one made up of a hydrophilic fiber, a thermally fusible bonding fiber or a strengthening assistant, and a superabsorbent polymer. The superabsorbent polymer is not present on the absorbent surface of the absorbent sheet for absorbing liquid but distributed inside the absorbent sheet, and adheres to the hydrophilic fiber constituting the absorbent sheet. The superabsorbent polymer is spread in an amount of 5 to 300 g/m$^2$ of the absorbent sheet and the absorbent sheet has a thickness of 0.3 to 1.5 mm.

A still preferred absorbing sheet 31 is composed of a fibrous structure made up of bulky hydrophilic fiber and thermally fusible bonding fiber or a strengthening assistant and superabsorbent polymer particles, in which the superabsorbent polymer particles do not exist on the absorbing surface of the absorbent sheet but are dispersed and fixed in the inside of the fibrous structure, and the superabsorbent polymer particles are spread in an amount of 20 to 70 g/m$^2$ of the absorbent sheet and the absorbent sheet has a thickness of 0.3 to 1.5 mm.

In such an absorbent sheet, since a superabsorbent polymer is fixedly dispersed in a single sheet in a three-dimensional pattern, the absorption ability of the superabsorbent polymer is effectively exhibited. Moreover, the gel blocking of the polymer is less. Accordingly, a body fluid tends to pass through the absorbent sheet smoothly. Thus, the absorbent sheet can advantageously be used in order to obtain a high absorption ability.

It is preferred that the barrier cuffs 40,40 each are 5 to 35 mm distant from the corresponding side edges of the top layer (It is preferred that the distance between the barrier cuff 40 and the top layer at the lateral side edge is 5 to 35 mm) If the distance is less than 5 mm, body fluid may flow beyond the barrier cuffs 40, 40 and may not be absorbed by the absorbent member and leakage tends to occur sideways. In contrast, if the distance is more than 35 mm, a distance $W_2$ between the two cuffs 40, 40 (distance from an outer edge of one of the barrier cuffs 40, 40 to an outer edge of the other barrier cuff 40) is difficult to be set in a satisfactory manner.

In order for the barrier cuffs 40, 40 not to give the perception of disorder to the wearer and in order for the absorbent sheet 31 to exhibit a favorable absorptive capacity of body fluid at the barrier cuffs 40, 40, the width $W_1$ of barrier cuffs 40, 40 are each preferably 5 mm to 25 mm. The distance $W_2$ between the barrier cuffs 40, 40 (distance from an outer edge of one of the barrier cuffs 40, 40 to an outer edge of the other barrier cuff 40) is preferably 20 mm to 70 mm. If the distance is less than 20 mm, a body fluid discharging portion of the wearer may be difficult to contact the part between the barrier cuffs 40, 40, and the body fluid may not be securely led to the pocket poriton. In contrast, if the distance is more than 70 mm, the part of the absorbent member 30 outside each of the barrier cuffs 40, 40 becomes too small to fully absorb the body fluid which flows beyond the barrier cuffs 40, 40. The result may be that body fluid tends to leak from the left and right side edges of the sanitary napkin 1. The barrier cuffs 40, 40 are each preferably 1 mm to 10 mm in thickness T. If the thickness T is less than 1 mm, there is the possibility that the leakage of body fluid cannot be effectively avoided. In contrast, if the thickness T is more than 10 mm, the perception of disorder is given to the wearer.

As the viscous agent for forming the viscous portions 25, 25 and as the peelable paper 60, any one selected from those which have heretofore been used can be selected with no special limitation.

In the sanitary napkin 1 according to this embodiment, the barrier cuffs 40, 40 contact the wearer, and body fluid is led to the pocket portion 50 located between the barrier cuffs 40, 40, where the body fluid is absorbed into the absorbent sheet 31 through the top layer 100. The unabsorbed body fluid deposited in the pocket portion 50 is prevented from flowing sideways by the barrier cuffs 40, 40 which function as leakage-preventive walls. Even in the event the body fluid flows over the barrier cuffs 40, 40 caused by an exceptionally large quantity of body fluid or extremely hard motion of the wearer, such body fluid may be absorbed by the absorbent member 30 located outside the barrier cuffs 40, 40.

In this way, according to the sanitary napkin 1 of this embodiment, body fluid is prevented from flowing out and being deposited in the pocket portion 50 owing to the pair of barrier cuffs 40, 40 arranged in the vicinity of the discharging portion when worn. Thus, the leakage of body fluid from the left and right side portions of the sanitary napkin 1 can be avoided even in case of a large quantity of body fluid and even in case of dynamic motion of the wearer.

Further, according to the sanitary napkin 1 of this embodiment, since body fluid which may flow over the barrier cuffs 40, 40 is absorbed at the outside of the barrier cuffs 40, 40, the leakage of body fluid from the left and right side portions of the sanitary napkin 1 can be avoided even in case of a large quantity of body fluid and even in case of dynamic motion of the wearer.

Furthermore, according to the sanitary napkin 1 of this embodiment, since the barrier cuffs 40, 40 are formed of the absorbent member 30, a large quantity of body fluid is absorbed also in the barrier cuffs 40, 40 and therefore, the leakage of body fluid from the left and right opposing side portions of the sanitary napkin 1 can effectively be prevented.

According to the sanitary napkin 1 of this embodiment, since the absorbent member 30 is the absorbent sheet 31 of 0.3 mm to 5 mm in thickness on the top layer 10, twisting seldom occurs, the perception of disorder is not given to the wearer, and a sufficient absorptive capacity of body fluid is exhibited.

According to the sanitary napkin 1 of this embodiment, the barrier cuffs 40, 40 are formed by folding the absorbent sheet 31 having a thickness of 0.3 mm to 5 mm and having a thickness equal to at least about 1 mm in combination with the top layer 10. Therefore, it is difficult for the body fluid to flow over the barrier cuffs 40, 40 and the possible leakage from the left and right opposing side portions of the sanitary napkin 1 can effectively be prevented.

According to the sanitary napkin 1 of this embodiment, the barrier cuffs 40, 40 are each formed by folding the absorbent sheet 31 having a thickness of 0.3 mm to 5 mm, and can be erected/deformed independently of other parts. Therefore, they nicely fit to the contacting portion of the wearer. Even if the back layer 20 is twisted together with the clothing, the barrier cuffs 40, 40 are not twisted, therefore, an improved absorptive capacity is ensured.

According to the sanitary napkin 1 of this embodiment, since the top layer 10 is folded and overlaid together with the absorbent sheet 31, the barrier cuffs 40, 40 can be more effectively erected/deformed independently of other parts, a body fluid finds it difficult to migrate to the left and right opposing side portions at the top layer 10 as well, and thus, the possible leakage of body fluid can be prevented in a more efficient manner.

According to the sanitary napkin 1 of this embodiment, the barrier cuffs 40, 40 are each developed in the longitudinal direction of the side edges of the sanitary napkin 1 and a recessed part between the barrier cuffs 40, 40 nicely fits the discharging portion of the wearer. Accordingly, the leakage preventive function of the barrier cuffs 40, 40 and the pocket portion 50 is effectively exhibited.

In order to obtain a favorable formation of each barrier cuff 40, the central portion 31a of the absorbent sheet 31 is preferably bonded to the back layer (or an auxiliary sheet which may be located below the absorbent sheet). It is also preferred that the inside of the barrier cuff 40 obtained by folding back the absorbent sheet 31 is fixed by an adhesive or the like. On the other hand, in order to enhance the softness and deformation of the barrier cuff 40, the central part 31a of the absorbent sheet 31 is not fixed and the inside of the barrier cuff 40 is not fixed by adhesive. In accordance with the purposes, the fixing state of each part can be selected.

Figure 3:
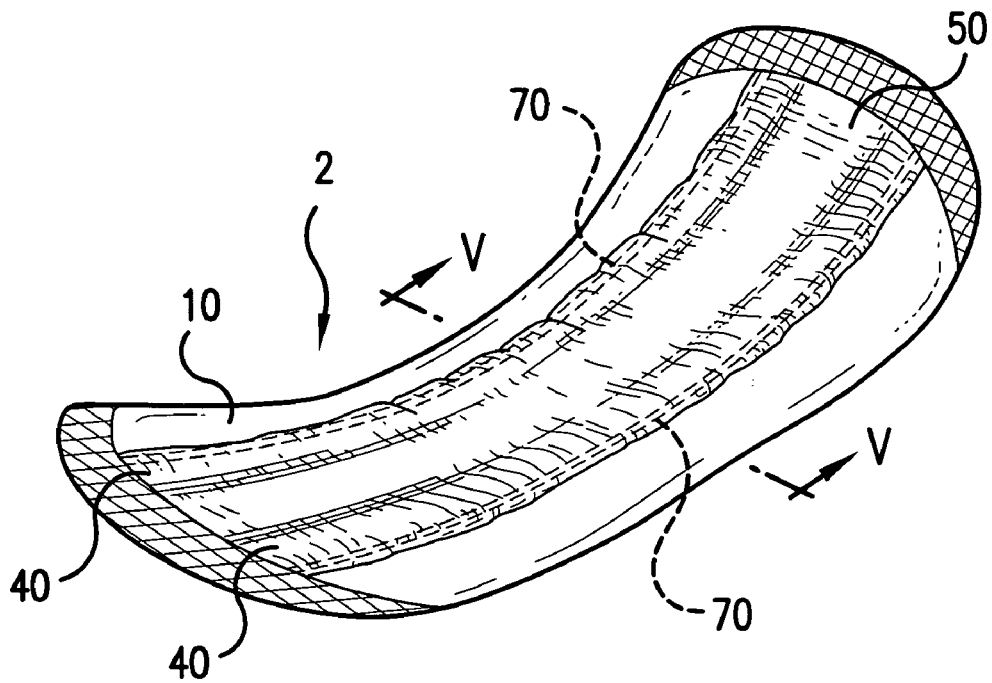
FIG. 3 is a perspective view showing an absorbent article according to the second embodiment of the present invention.
Figure 4:
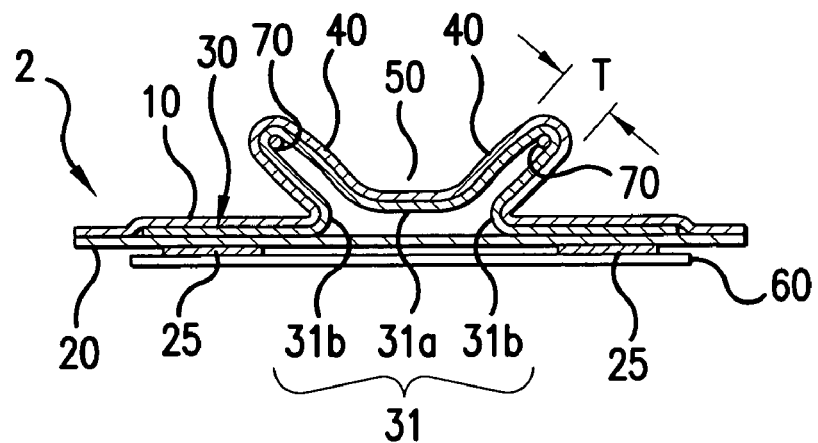
FIG. 4 is a sectional view taken along line V—V of FIG. 3, and viewed in a direction as indicated by arrows.

FIG. 3 is a perspective view showing a second embodiment of a sanitary napkin according to the absorbent article of the present invention, and FIG. 4 is a sectional view taken along line V—V of FIG. 3 and viewed in a direction as indicated by arrows. In this embodiment, those members identical with the first embodiment of FIGS. 1 and 2 are denoted by identical reference numerals, with the description thereof being omitted.

As shown in FIGS. 3 and 4, in a sanitary napkin 2 of this embodiment, a pair of elastic members 70, 70 are provided inside side edges of the barrier cuffs 40, 40 located along the longitudinal direction of the barrier cuffs 40, 40 such that the barrier cuffs 40, 40 are shrunk along the longitudinal direction thereof over a prescribed length.

This embodiment is now described in more detail. In this embodiment, the elastic members 70, 70 are, in their expanded states, fixedly secured at the folded portions between the central portion 31a and the side portions 31b, 31b of the absorbent sheet 31, approximately over the entire length from the side of a back layer 20. By the shrinkage of the elastic members 70, 70, the folded portions are projected in the upward direction.

As the elastic members 70, 70, a film, fiber, a foamed body and the like composed of a polymer of a number of rubbers, such as polyurethanes, polybutadiene, isoprene and the like, ethylene-vinyl acetate, and a number of polyolefins having extensibility can be used. In order to exhibit a favorable effect without degrading the comfortable wearing perception, the elastic members 70, 70 are preferably 10 gf to 300 gf in stress at 30% expansion.

The elastic members 70, 70 are not particularly limited in position and length for arrangement. However, in order to bend the barrier cuffs 40, 40 such that they favorably comply with the wearer, the elastic members 70, 70 are preferably arranged over a length of 15% to 90% of the entire longitudinal length of the sanitary napkin 2.

All the construction other than the arrangement of the elastic members 70, 70 of this embodiment is the same as the afore-mentioned first embodiment.

The absorbent sheet 31 is preferably 0.3 mm to 5 mm in thickness, more preferably 0.3 mm to 3 mm, and most preferably 0.3 mm to 1.5 mm as in the afore-mentioned first embodiment. Those sheets usable as the absorbent sheet 31, preferred sheets and material thereof are also the same as in the afore-mentioned first embodiment.

The sanitary napkin 2 of this embodiment can also provide the same function and effect as in the first embodiment.

According to the sanitary napkin 2 of this embodiment, since the barrier cuffs 40, 40 each include an absorbent sheet 31 having a thickness of 0.3 mm to 5 mm, the elastic members 70, 70 can easily be secured to the inside of the barrier cuffs 40, 40.

According to the sanitary napkin 2 of this embodiment in particular, the absorbent sheet 31 is shrunk by the elastic member 70,70 over a prescribed length in the longitudinal direction, so that the sanitary napkin 2 is bent, as shown in FIG. 4, in the longitudinal direction in such a way as to comply with contacting part of the weaer, and the barrier cuffs 40, 40 are held in their upstanding postures on the wearer's skin side. Thus, since a more highly three-dimensional and more nicely fitting pocket 50 is formed, a possible leakage of body fluid can more effectively be prevented.

According to the sanitary napkin 2 of this embodiment, since the elastic members 70, 70 are secured to the thin absorbent sheet 31, the frill-like irregularities formed at the barrier cuffs 40, 40 by shrinkage of the elastic members 70, 70 are comparatively small. Also, the good touch to the wearer's skin is hardly degraded on the side of the top layer 10, and comfortable wearing is maintained.

Figure 5:
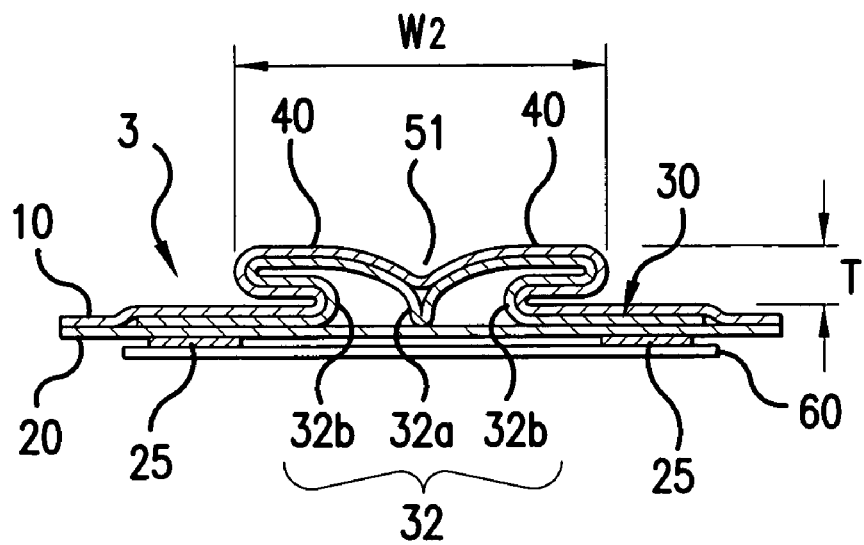
FIG. 5 is a sectional view, corresponding to FIG. 2 of the first embodiment, showing an absorbent article according to a third embodiment of the present invention.

FIG. 5 is a sectional view, corresponding to FIG. 2 of the first embodiment, showing a sanitary napkin as the third embodiment of an absorbent article of the present invention. In this embodiment, those members identical with the first embodiment of FIGS. 1 and 2 are denoted by identical reference numerals, and description thereof is omitted.

As shown in FIG. 5, in a sanitary napkin 3 of this embodiment, side portions 32b,32b of an absorbent sheet 32 are folded inwardly to the side of the back layer 20 at the left and right opposing side edges of the central portion 32a and then folded back outwardly to form an overlaid configuration at the left and right opposing side portions of the central portion 32a. A pair of folded portions thus formed are arranged opposite and proximate to each other on the back layer 20 side of the central portion 32a. The barrier cuffs 40, 40 are continuously formed. The central portion 32a is folded in such a way as to form a convex configuration on the back layer side, thereby forming a pocket portion 51 having a V-shape in sectional view. The capacity of the pocket portion 51 is smaller than that in the first embodiment.

All the construction other than the folded form of the absorbent sheet 32 and the pocket portion 51 of this embodiment is the same as the aforementioned first embodiment.

The absorbent sheet 32 is preferably 0.3 mm to 5 mm in thickness, more preferably 0.3 mm to 3 mm, and most preferably 0.3 mm to 1.5 mm as in the afore-mentioned first embodiment. Those sheets usable as the absorbent sheet 31, preferred sheets and material thereof are also the same as in the afore-mentioned first embodiment. The distance $W_2$ between the barrier cuffs 40, 40 is preferably 20 mm to 70 mm and the thickness T of the barrier cuffs 40, 40 is preferably 1 mm to 10 mm as in the first embodiment.

The sanitary napkin 3 of this embodiment can also provide the same function and effect as in the first embodiment.

According to the sanitary napkin 3 of this embodiment, the barrier cuffs 40, 40 are each developed in the longitudinal direction of the side edges of the sanitary napkin 3 and a recessed part between the barrier cuffs 40, 40 nicely fits the discharging portion of the wearer. Accordingly, the leakage preventive function of the barrier cuffs 40, 40 and the pocket portion 50 is remarkably effectively exhibited.

Figure 6:
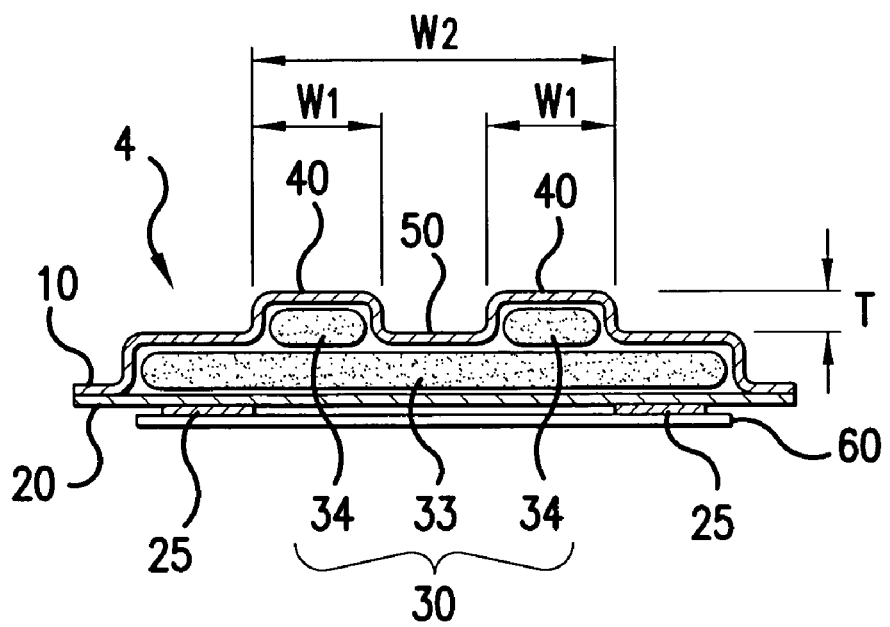
FIG. 6 is a sectional view, corresponding to FIG. 2 of the first embodiment, showing an absorbent article according to a fourth embodiment of the present invention.

FIG. 6 is a sectional view, corresponding to FIG. 2 of the first embodiment, showing a sanitary napkin as the fourth embodiment of an absorbent article of the present invention. In this embodiment, those members identical with the first embodiment of FIGS. 1 and 2 are denoted by identical reference numerals, with the description thereof being omitted.

As shown in FIG. 6, in the sanitary napkin 4 of this embodiment, the absorbent member 30 consists of a lower-layer absorbent pad 33, and upper-layer absorbent pads 34, 34. The lower-layer absorbent pad 33 is of a plate-like configuration extending from the vicinity of one of the opposing side edges of the back layer 20 to the vicinity of the other side edge, while the upper-layer absorbent pads 34, 34 are each like a rod with rectangular configuration in vertical sectional view. The upper-layer absorbent pads 34, 34 are located away from each other on one surface of the lower-layer absorbent pad 33 in the longitudinal direction of the sanitary napkin 4. The parts of aforementioned surface of the lower-layer absorbent pad 33 and the surfaces of the upper-layer absorbent pads 34, 34, which are exposed without contacting each other, are lapped with the top layer 10. Thus, the barrier cuffs 40, 40 are formed by the upper-layer pads 34, 34 and the top layer 10. In other words, the absorbent member 30 includes two pads (upper-layer absorbent pads 34,34) supported by a planar pad (lower-layer absorbent pad 33), each pad supports the top layer 10 so that the two pads form the barrier cuffs 40,40.

As the lower-layer absorbent pad 33 and upper-layer absorbent pads 34, 34, those, which have heretofore been used, can be used without any particular limitation.

This embodiment is the same as the first embodiment except that the absorbent member 30 consists of the lower-layer absorbent pad 33 and the upper layer absorbent pads 34, 34 and the covering state of the absorbent member 30 with the top layer 10 is different.

The barrier cuffs 40, 40 are each preferably 5 mm to 25 mm in width $W_1$. The distance $W_2$ between the barrier cuffs 40, 40 is preferably 20 mm to 70 mm and the thickness T of the barrier cuffs 40, 40 is preferably 1 mm to 10 mm as in the first embodiment.

The sanitary napkin 4 of this embodiment can also provide the same function and effect as the sanitary napkin 1 of the first embodiment.

Figure 7:
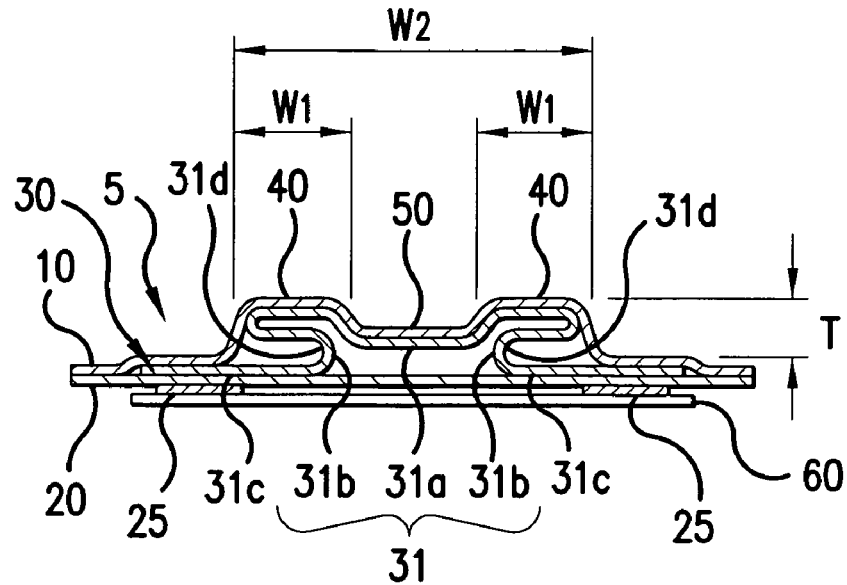
FIG. 7 is a sectional view, corresponding to FIG. 2 of the first embodiment, showing an absorbent article according to a fifth embodiment of the present invention.

FIG. 7 is a sectional view, corresponding to FIG. 2 of the first embodiment, showing a sanitary napkin as the fifth embodiment of an absorbent article of the present invention. In this embodiment, those members identical with the first embodiment of FIGS. 1 and 2 are denoted by identical reference numerals, and description thereof is omitted.

As shown in FIG. 7, in the sanitary napkin 5 of this embodiment, the entire surface of the absorbent sheet 31 is not overlaid on the top surface 10 and only the surface of the folded absorbent sheet 31, which surface is exposed without being folded, is overlaid on the top layer 10. In other words, the absorbent member 30 includes the absorbent sheet 31, the absorbent sheet 31 is folded in an overlapping serpentine configuration, the serpentine configuration includes curved portions 31*d*,31*d* spaced apart from planar portions 31*c*,31*c* of the sheet, the top layer 10 covers the serpentine configuration so that the curved portions 31*d*,31*d* and planar portions 3.1*c*,31*c* of the absorbent sheet and portions of the top layer 10 form enclosed volumes of empty space.

All the construction other than the arrangement form of the top layer 10 of this embodiment is the same as the aforementioned first embodiment.

The absorbent sheet 31 is preferably 0.3 mm to 5 mm in thickness, more preferably 0.3 mm to 3 mm, and most preferably 0.3 mm to 1.5 mm as in the afore-mentioned first embodiment. Those sheets usable as the absorbent sheet 31, preferred sheets and material thereof are also the same as in the afore-mentioned first embodiment. The barrier cuffs 40, 40 are preferably 5 mm to 25 mm in width $W_1$. The distance $W_2$ between the barrier cuffs 40, 40 is preferably 20 mm to 70 mm and the thickness T of the barrier cuffs 40, 40 is preferably 1 mm to 10 mm as in the first embodiment.

The sanitary napkin 5 of this embodiment can also provide the same function and effect as in the first embodiment.

According to the sanitary napkin 5 of this embodiment, the barrier cuffs 40, 40 are each developed in the longitudinal direction of the side edges of the sanitary napkin 5 and therefore, an inner side wall of the pocket portion 50 forms a rounded recess between the barrier cuffs 40, 40, which nicely fits the discharging portion of the wearer.

Figure 8:
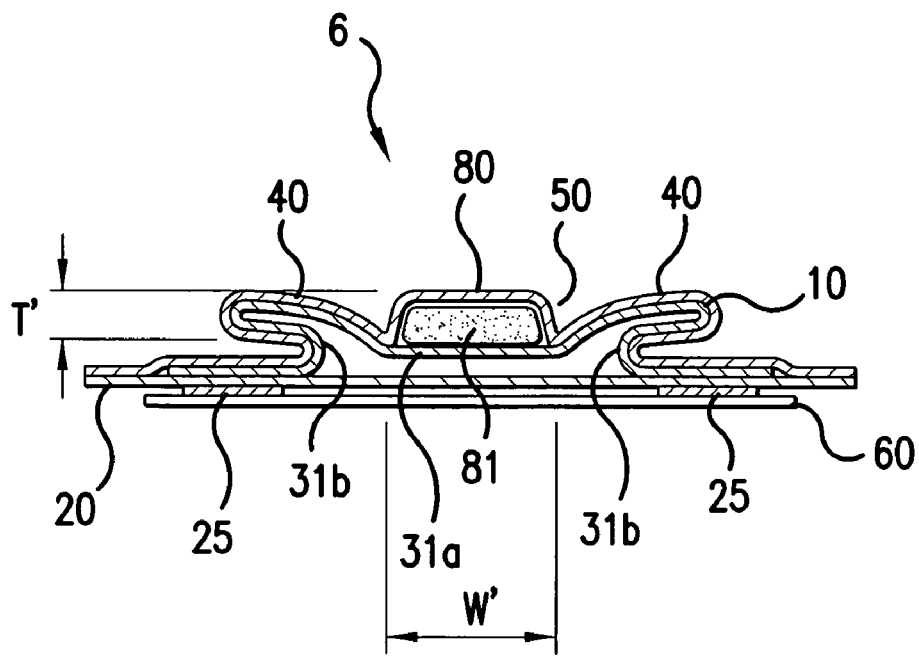
FIG. 8 is a sectional view, corresponding to FIG. 2 of the first embodiment, showing an absorbent article according to a sixth embodiment of the present invention.

FIG. 8 is a sectional view, corresponding to FIG. 2 of the first embodiment, showing a sanitary napkin as the sixth embodiment of an absorbent article of the present invention. In this embodiment, those members identical with the first embodiment of FIGS. 1 and 2 are denoted by identical reference numerals, with the description thereof being omitted.

As shown in FIG. 8, in the sanitary napkin 6 of this embodiment, the sanitary napkin 6 has a projecting portion 80 between the barrier cuffs 40,40 and on the skin contacting surface side of the pocket portion 50 along the longitudinal direction of the barrier cuffs 40, 40.

The projecting portion 80 is obtained by overlaying an absorbent body 81 on the central portion of the absorbent sheet and covering the absorbent sheet and the absorbent body 81 with the top layer from above. In other words, the absorbent member 30 includes the absorbent sheet 31 supporting an absorbent pad (absorbent body 81), the absorbent pad is disposed between the barrier cuffs 40,40, the absorbent sheet 31 is disposed between the absorbent pad and the back layer 20.

The projecting portion 80 is preferably 2 mm to 30 mm in thickness T' and 10 mm to 45 mm in width W' so that it nicely fits to the wearer's crotch portion.

The absorbent body 81 may be a folded absorbent sheet with an appropriate thickness by folding a sheet material which forms absorbent sheet 31, or be an absorbent pad.

The sanitary napkin 6 of this embodiment can provide, in addition to the same function and effect as in the first embodiment, an advantage in that leakage can be more effectively prevented, because the projecting portion 80 contacts the wearer's crotch portion and body fluid is absorbed directly by the projecting portion 80. Moreover, since the central portion in the longitudinal direction is rigidly increased by the projecting portion 80, twisting can be prevented. Furthermore, since the projecting portion 80 includes the absorbent body 81, higher absorption performance can be exhibited, which also serves to prevent leakage of body fluids in a more efficient manner.

The present invention should not be limited to the above-mentioned embodiments. The specific shape, dimension, etc. of each member can appropriately be modified without departing from the spirit and scope of the present invention.

For example, it is also acceptable that, in the above respective embodiments, that an auxiliary sheet, which consists of the sheet identical to the absorbent sheet 31,32, be provided on the back layer 20 side of the absorbent sheet 31,32 or the lower layer absorbent pad 33, so that the absorptive capacity should be increased in the vicinity of the back layer 20. This auxiliary sheet can be extended outside the absorbent sheet 31, 32.

In the above respective embodiments, the absorbent sheet 31 is obtained by folding side portions 31b, 31b, 32b, 32b of the sheet, which consists of the central portion 31a and side portions 31b, 31b connected to the opposing sides of the central portion 31a, to the top layer 10 side of the central portions 31a, 32a.

Figure 9:
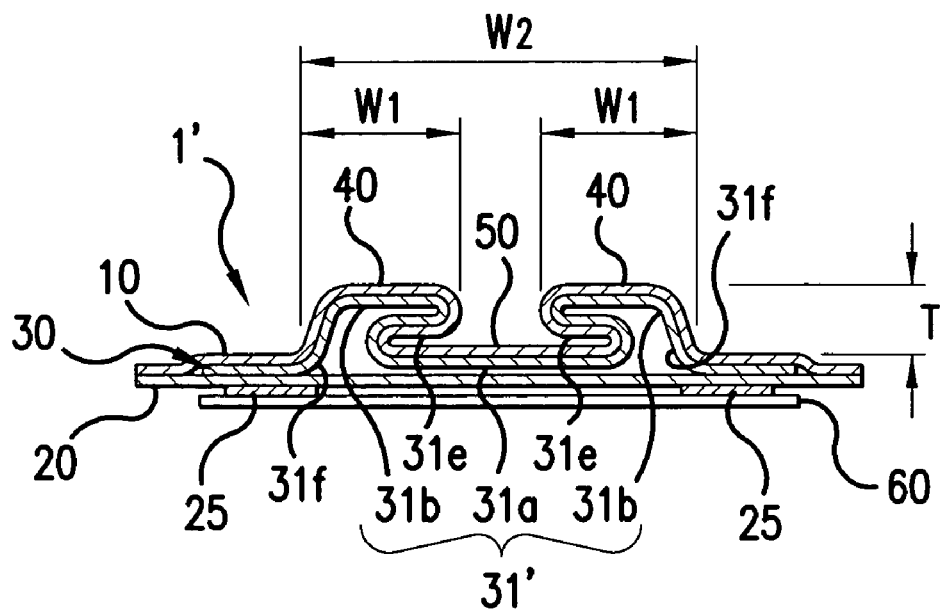
FIG. 9 is a sectional view, corresponding to FIG. 2 of the first embodiment, showing an absorbent article according to another embodiment of the present invention.

As such a sanitary napkin, FIG. 9 shows a sanitary napkin 1' which is provided with an absorbent sheet 31' in the first embodiment of FIGS. 1 and 2, the side portions 31b, 31b and the absorbent sheet 31' are folded inwardly at the left and right opposing side edges of the central portion 31a and overlaid on the top layer 10 on the left and right opposing side portions of the central portion 31a, and thereafter, folded back again so as to extend outward the central portion 31a, and the free edge portions of the respective side portions 31b, 31b are arranged in the vicinity of the left and right opposing side edges of the top layer 10. In the sanitary napkin 1' shown in FIG. 9, the absorbent member 30 includes the absorbent sheet 31, the absorbent sheet 31 is folded in the overlapping serpentine configuration 31e,31e, each barrier cuff 40 includes portions of the serpentine configuration 31e,31e that are disposed within the pocket portion 50 and curved non-overlapping portions 31f,31f which are disposed outside the pocket portion 50.

In each of the above embodiments, the absorbent sheets 31, 32 may be folded again inwardly from the vicinity of the side edges of the back layer 20 and overlaid one upon another, the sheets 31, 32 can provide the same effect as the aforementioned auxiliary sheet.

In each of the above embodiments, the side portions 31b, 31b, 32b, 32b of the absorbent sheets 31, 32 may be more folded and overlaid one upon another than done in the above embodiments, so that the barrier cuffs 40, 40 each have more multilayer structures.

In each of the above embodiments, the multilayered structure of the barrier cuffs 40, 40 may be formed by a plurality of absorbent sheets. In case of this arrangement, the absorbent sheets may be simply overlaid, adhered under pressure over their opposing entire surfaces to each other or partial surfaces by adhesive agent or the like.

In each of the above embodiments, it is also acceptable that the side edge portions of the back layer 20 are extended on the outward side of the absorbent member 30 to form leakage-preventive walls. Alternatively, leakage-preventive materials having liquid-impermeable properties can be arranged so that possible leakage of body fluid is more reliably prevented. The leakage-preventive walls and the leakage-preventive materials may be disposed between the absorbent member 30 and the top layer 10, or they may be arranged outward the top layer 10. In these cases, by covering the outside of the absorbent article with the liquid-impermeable material, by, for example, arranging the side edge portions of the back layer 20 outward the top layer 10, the barrier cuffs 40, 40 can more effectively prevent the oozing and side-leakage of body fluid from the absorbent member 30.

When the leakage-preventive walls and leakage-preventive materials are arranged by firmly attaching the top layer 10 and the leakage-preventive walls, or the leakage-preventive materials to the back layer 20 by heat fusion bonding at the perimeter of the absorbent member 30, the leakage-preventive walls or the leakage-preventive materials are held in their slightly erected postures so that a more favorable effect can be obtained. FIG. 2 shows one example, in which the leakage-preventive walls 20', 20' are obtained by extending the side edge portions of the back layer 20 of the first embodiment and arranging outward the top layer 10, as indicated by a dotted line of FIG. 2.

In the second embodiment, a liquid-shrinkable member capable of shrinking by absorbing liquid may be used as the elastic members 70, 70.

In the first embodiment of FIGS. 1 and 2, in the second embodiment of FIGS. 3 and 4, and in the third embodiment of FIGS. 5 and 6, the absorbent sheets 31, 32 and the top layers 10 may be formed into a single sheet.

Figure 10:
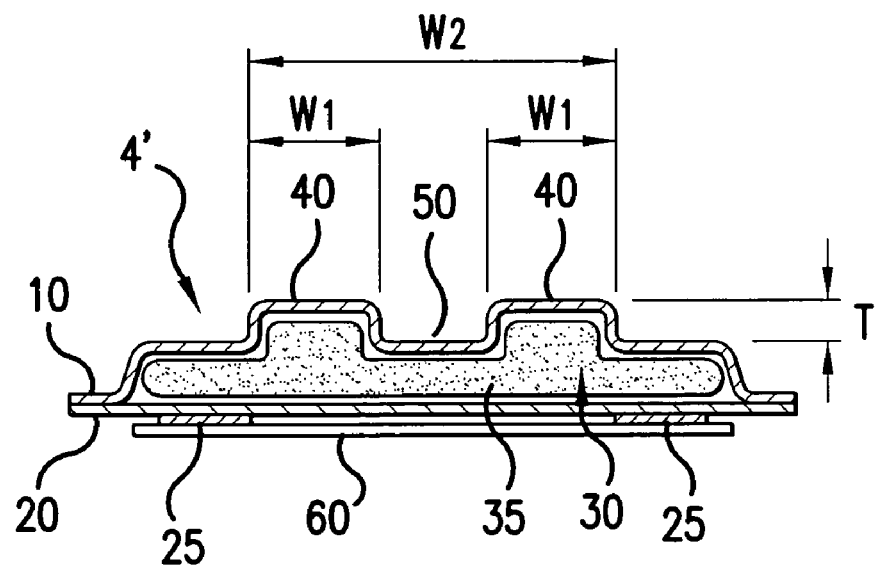
FIG. 10 is a sectional view, corresponding to FIG. 2 of the first embodiment, showing an absorbent article according to another embodiment of the present invention.

As shown in FIG. 10, in the fourth embodiment, an absorbent pad 35 with a barrier cuff, in which the lower-layer absorbent pad 33 and the upper-layer absorbent pads 34, 34 are integrally formed, may be used as the absorbent member 30. That is, in the sanitary napkin 4' shown in FIG. 10, the absorbent member 30 includes a planar pad (lower-layer absorbent pad 33) with integrally formed pad projections (upper-layer absorbent pads 34,34) extending from the planar pad, the projections form the barrier cuffs 40,40.

Figure 11:
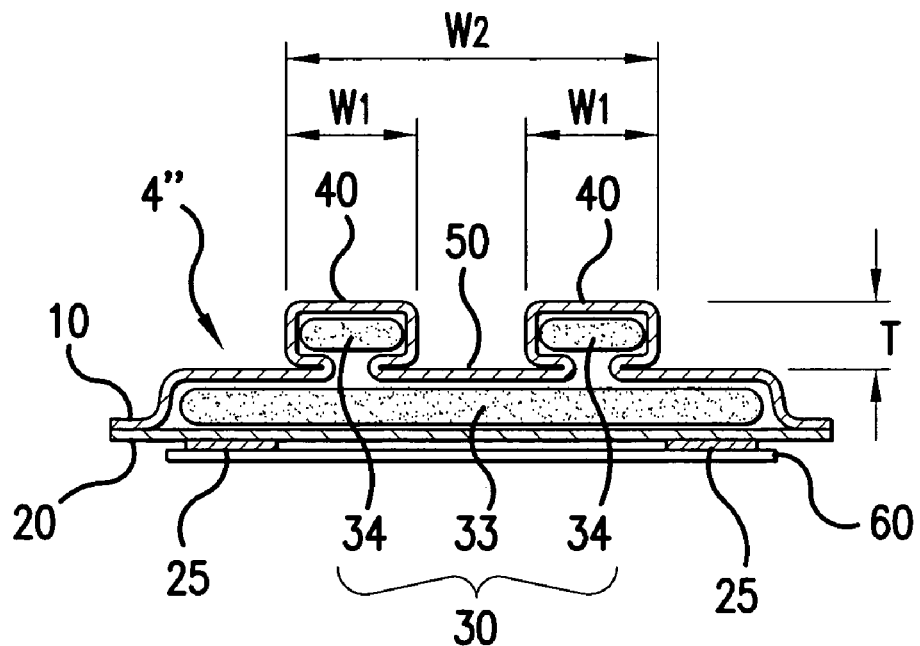
FIG. 11 is a sectional view, corresponding to FIG. 2 of the first embodiment, showing an absorbent article according to another embodiment of the present invention.

As shown in FIG. 11, in the fourth embodiment, the top layer 10 may be interposed between the lower-layer absorbent pad 33 and the upper-layer absorbent pads 34, 34 in such a manner that the barrier cuffs 40, 40 can be erected and deformed more independently of other parts. Owing to this arrangement, the barrier cuffs 40, 40 can more nicely fit to the contacting portion of the wearer. That is, in the sanitary napkin 4" shown in FIG. 11, the absorbent member 30 includes two pads (upper-layer absorbent pads 34,34) and a planar pad, (lower-layer absorbent pad 33), each pad is substantially enclosed by the top layer 10 so that the two pads form the barrier cuffs 40,40, the top layer substantially spaces the two pads from the planar pad.

Figure 12:
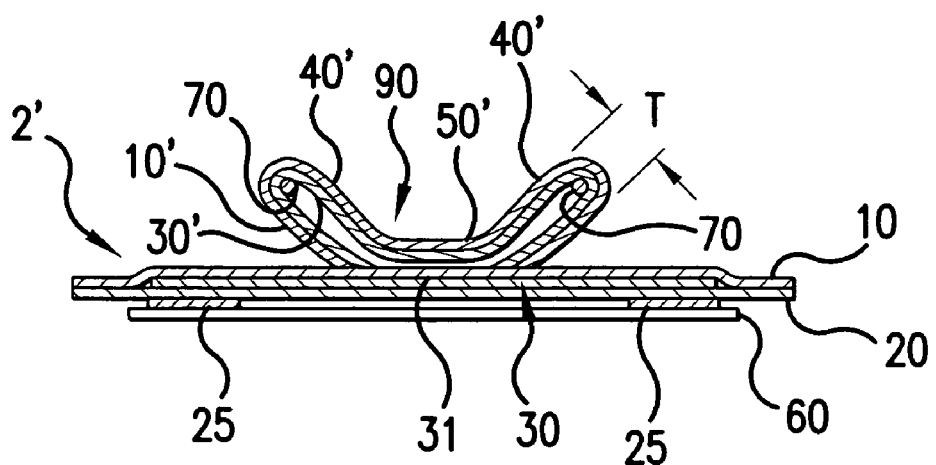
FIG. 12 is a sectional view, corresponding to FIG. 2 of the first embodiment, showing an absorbent article according to another embodiment of the present invention.

Also, by securing a separate body having a pair of barrier cuffs and a pocket therebetween to the skin contacting surface side of the top layer of the conventional sanitary napkin, the barrier cuffs and the pocket portion as in each of the above embodiments can be formed. FIG. 12 shows one example, in which a separate body 90 having a pair of barrier cuffs 40', 40' and a pocket portion 50' therebetween is secured to the skin contacting side of the top layer 10' so as to realize the same sanitary napkin 2' as in the second embodiment. The barrier cuffs 40', 40' can be formed of a single sheet consisting of the absorbent sheet and the top sheet.

That is, the sanitary napkin 2' shown in FIG. 12 comprises:
    the first liquid-permeable top layer 10;
    the liquid impermeable back layer 20,
    the first liquid retentive absorbent member 30 interposed between the first liquid-permeable top layer 10 and the liquid impermeable back layer 20,
    the second liquid-permeable top layer 10'; and
    the second liquid retentive absorbent member 30' interposed between the second liquid-permeable top layer 10' and the first liquid-permeable top layer 10; the second liquid retentive absorbent member including an opposing pair of barrier cuffs 40',40' which are within longitudinal edges of the first liquid-retentive top layer 10 and extend along longitudinal edges of the first liquid-retentive top payer 10, and the pocket portion 50 formed between the pair of barrier cuffs 40',40'.

The barrier cuffs are each preferably 1 mm to 30 mm in thickness T when worn (including the states that the barrier cuffs are slightly erected/deformed by absorption of body fluid and that the barrier cuffs are erected by the elastic members).

The overlaid configuration of the absorbent sheet, the covering fashion of the absorbent sheet with the top layer, presence or absence of the elastic members, presence or absence of the projecting portion, etc. can be selectively employed in each of the above embodiments. It is also preferable to interpose a sheet, such as a mount and a non-woven fabric, between the top layer and the absorbent sheet. Owing to this arrangement, the absorption performance can be enhanced.

Figure 13:
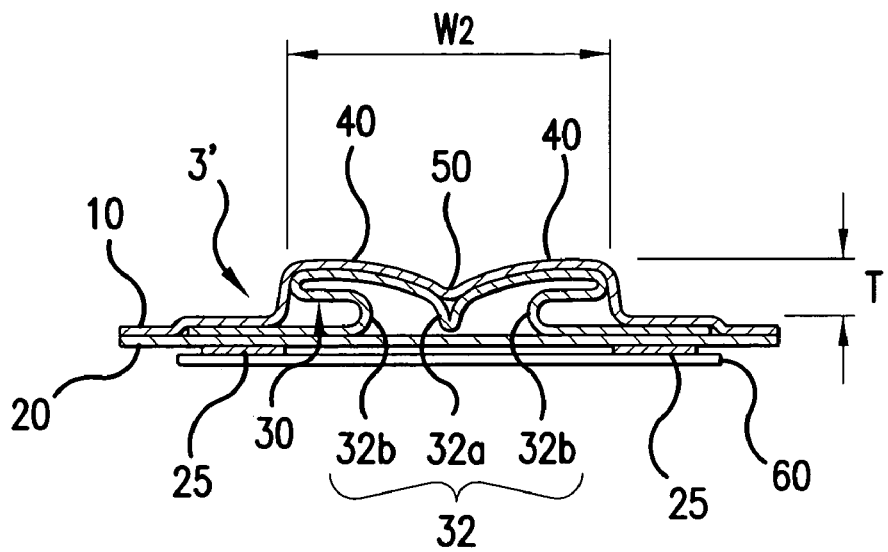
FIG. 13 is a sectional view, corresponding to FIG. 2 of the first embodiment, showing an absorbent article according to another embodiment of the present invention.

For example, as shown in FIG. 13, the third embodiment of FIG. 5 may be arranged such that only the exposed surface, which is not folded, of the folded absorbent sheet 31 is overlaid on the top layer 10, instead of the entire surface of the absorbent sheet 31 being overlaid. As is in the embodiment shown in FIG. 5, the pocket portion 50 has a cross section which is substantially V-shaped.

Figure 14:
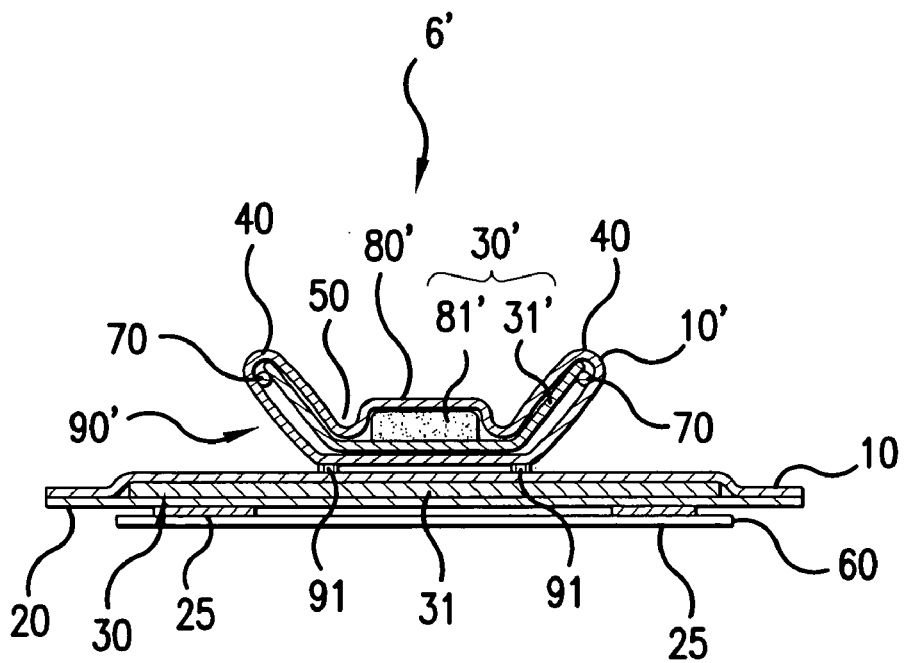
FIG. 14 is a sectional view, corresponding to FIG. 2 of the first embodiment, showing an absorbent article according to another embodiment of the present invention.

An embodiment whose cross section corresponding to FIG. 2 has a configuration shown in FIG. 14 is another embodiment of the absorbent article of the present invention.

The sanitary napkin 6' shown in FIG. 14 comprises:
the first liquid-permeable top layer 10;
the liquid impermeable back layer 20;
the first liquid retentive absorbent member 30 interposed between the first liquid-permeable top layer 10 and the liquid impermeable back layer 20;
the second liquid-permeable top layer 10';
the second liquid retentive absorbent member 30' is enclosed by the second liquid-permeable top layer 10', the second liquid retentive absorbent member includes a pad (absorbent sheet 31') and an auxiliary pad (absorbent body 81'), the second liquid retentive absorbent member including an opposing pair of barrier cuffs 40,40 which are within longitudinal edges of the first liquid retentive top layer 10 and extend along longitudinal edges of the first liquid retentive top layer 10, and the pocket portion 50 formed between the pair of barrier cuffs 40,40, and means 91,91 for securing the first liquid-permeable top layer 10 to the second liquid-permeable top layer 10'.

In the sanitary napkin 6' shown in FIG. 14, a separate body 90' having a pocket portion 50 between the pair of barrier cuffs 40, 40 is secured to the skin contacting surface side of the top layer of the sanitary napkin 6' by an adhesive agent. The absorbent sheet 31' of the separate body 90' are is not overlaid in the barrier cuffs 40, 40, and the elastic members 70, 70 are each located outward the absorbent sheet 31'. A projecting portion 80' is obtained by interposing a conventional absorbent body 81' comprising a mount, a nonwoven fabric, a pulp, a liquid-absorbent polymer and the like, between the absorbent sheet 31' of the separate body 90' and the top layer 10'. In the embodiment shown in FIG. 14, the same explanation as given in the above-mentioned embodiments is applicable to the constitution and composing materials to which the specific explanation has not been given.

Also, as shown in FIG. 14, a separate body 90' having a pocket portion 50 between the pair of barrier cuffs 40,40 is secured to the skin-contacting surface side of the top layer of the conventional sanitary napkin by means 91,91 which is an adhesive agent or the like.

Figure 15:
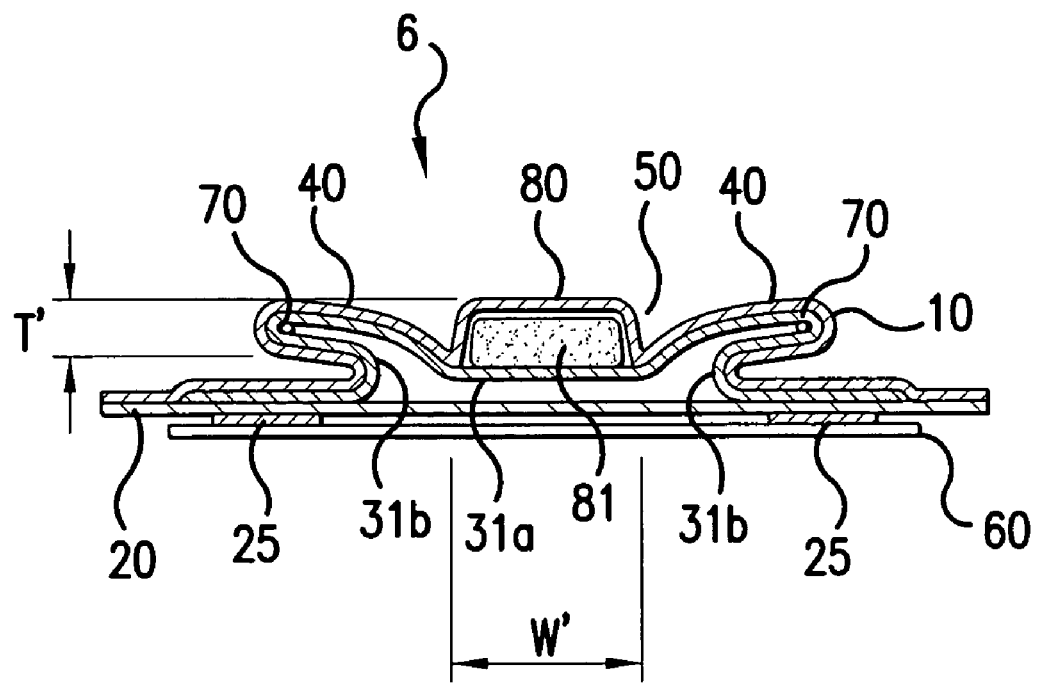
FIG. 15 is a sectional view, corresponding to FIG. 8 of the sixth embodiment showing an absorbent article according to another embodiment of the present invention.

Furthermore, the fourth embodiment of FIG. 6, the fifth embodiment of FIG. 7 and the sixth embodiment of FIG. 8, and so forth, may include the same elastic members 70 as in the second embodiment of FIGS. 3 and 4. For example, FIG. 15 illustrates the sixth embodiment, which includes elastic members 70.

The absorbent article may be those other than the sanitary napkin, such as an incontinent pad and a breast-feeding pad.

INDUSTRIAL APPLICABILITY

As described hereinbefore, according to the absorbent article of the present invention, the possible leakage of body fluid can effectively be prevented from the left and right opposing side portions of the absorbent article irrespective of the quantity of body fluid and the motion of the wearer because body fluid is prohibited to flow out by a pair of barrier cuffs arranged in the vicinity of the discharging portion when worn and by the pocket portion, and body fluid, which happens to flow over the barrier cuffs, is also absorbed outward the barrier cuffs.

Further, according to the absorbent article of the present invention, since the barrier cuffs are each formed of the absorbent member, a large quantity of body fluid is also absorbed at the barrier cuffs. Thus, the possible leakage of body fluid can effectively be prevented from the left and right opposing side portions of the absorbent article.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:
1. An absorbent article comprising:
a liquid-permeable top layer;
a liquid-impermeable back layer;
a liquid retentive absorbent member, interposed entirely between said top layer and said back layer, said absorbent member being arranged to form (a) an opposing pair of barrier cuffs which are within longitudinal edges of said top layer and extend along the longitudinal edges, said absorbent member comprising an absorbent sheet, said pair of barrier cuffs being formed by integrally folding only the absorbent sheet and said top layer, and (b) a pocket portion formed between said pair of barrier cuffs; and
a projecting portion located between said barrier cuffs on a skin contactable surface side of said pocket portion along the longitudinal direction of said barrier cuffs, said projecting portion being formed by an absorbent pad, and
wherein said absorbent sheet has a thickness of 0.3 mm to 5 mm.

2. The absorbent article according to claim 1, wherein said barrier cuffs are 1 mm to 10 mm in thickness.

3. The absorbent article according to claim 1, wherein said barrier cuffs are arranged away from each other, and elastic members are provided at inward side edges of said barrier cuffs located along the longitudinal direction of said barrier cuffs such that said barrier cuffs are shrunk along the longitudinal direction of said barrier cuffs over a prescribed length.

4. The absorbent article according to claim 1, wherein said absorbent sheet of said barrier cuffs is folded in an overlapping, serpentine configuration.

5. The absorbent article according to claim 1, wherein said absorbent sheet comprises a superabsorbent polymer interposed between a pair of papers, nonwoven fabrics or a combination thereof, or an admixture of a hydrophilic fiber, a superabsorbent polymer and a binder, wherein the admixture is in a sheet-like shape.

6. The absorbent article of claim 1, wherein said absorbent member includes means for bonding portions adjacent to said barrier cuffs to said back layer, and said barrier cuffs are spaced apart from said back layer.

7. The absorbent article of claim 6, wherein said means for bonding portions adjacent to said barrier cuffs to said back layer includes the application of at least one of an adhesive agent and heat sealing agent between the portion adjacent to said barrier cuff and said back layer.

8. The absorbent article of claim 1, wherein said absorbent article includes means for bonding said top layer to said liquid retentive absorbent member.

9. The absorbent article of claim 8, wherein said means for bonding said top layer to said liquid retentive member includes the application of at least one of an adhesive agent and heat sealing agent between said top layer and said liquid retentive layer.

10. The absorbent article of claim 1, wherein said absorbent sheet supports said absorbent pad, and said absorbent sheet is disposed between said absorbent pad and said back layer.

11. The absorbent article according to claim 1, wherein said barrier cuffs are located at a spaced location from longitudinal edges of said absorbent member.

12. The absorbent article according to claim 1, wherein said absorbent member does not extend to the longitudinal edges of said top layer.

13. An absorbent article comprising:
a first liquid-permeable top layer;
a liquid impermeable back layer;
a first liquid retentive absorbent member interposed entirely between said first liquid-permeable top layer and said liquid impermeable back layer;
a second liquid-permeable top layer;
a second liquid retentive absorbent member interposed between said second liquid-permeable top layer and said first liquid-permeable top layer, said second liquid retentive absorbent member including an opposing pair of barrier cuffs which are within longitudinal edges of said first liquid-permeable top layer and extend along longitudinal edges of said first liquid-permeable top layer, said absorbent member comprising an absorbent sheet, said pair of barrier cuffs being formed by integrally folding only the absorbent sheet and said second liquid permeable top sheet, and a pocket portion is formed between said pair of barrier cuffs; and
a projecting portion located between said barrier cuffs on a skin contactable surface side of said pocket portion along the longitudinal direction of said barrier cuffs.

14. The absorbent article according to claim 13, wherein said barrier cuffs are located at a spaced location from longitudinal edges of said first absorbent member.

15. The absorbent article according to claim 13, wherein said second absorbent member does not extend to the longitudinal edges of said first top layer.

16. An absorbent article comprising:
a first liquid-permeable top layer;
a liquid impermeable back layer;
a first liquid retentive absorbent member interposed entirely between said first liquid-permeable top layer and said liquid impermeable back layer;
a second liquid-permeable top layer;
a second liquid retentive absorbent member enclosed by said second liquid-permeable top layer, said second liquid retentive absorbent member includes a pad and an auxiliary pad, said second liquid retentive absorbent member including an opposing pair of barrier cuffs which are within longitudinal edges of said first liquid-permeable top layer and extend along longitudinal edges of said first liquid-permeable top layer, said pair of barrier cuffs being formed by integrally folding only said pad and said second liquid-permeable top sheet, and a pocket portion is formed between said pair of barrier cuffs;
means for securing said second liquid-permeable top layer to said first liquid-permeable top layer; and
a projecting portion located between said barrier cuffs on a skin contactable surface side of said pocket portion along the longitudinal direction of said barrier cuffs, said projecting portion being formed by said auxiliary pad.

17. The absorbent article according to claim 16, wherein said barrier cuffs are located at a spaced location from longitudinal edges of said first absorbent member.

18. The absorbent article according to claim 16, wherein said second absorbent member does not extend to the longitudinal edges of said first top layer.

* * * * *